US00PP29370P3

(12) United States Plant Patent
Finn

(10) Patent No.: US PP29,370 P3
(45) Date of Patent: Jun. 12, 2018

(54) STRAWBERRY PLANT NAMED 'MARYS PEAK'

(50) Latin Name: ***Fragaria xananassa* Duchesne ex Rozier**
Varietal Denomination: Marys Peak

(71) Applicant: The United States of America, as represented by the Secretary of Agriculture, Washington, DC (US)

(72) Inventor: Chad E Finn, Corvallis, OR (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days. days.

(21) Appl. No.: 15/330,507

(22) Filed: Sep. 29, 2016

(65) Prior Publication Data

US 2018/0092268 P1 Mar. 29, 2018

(51) Int. Cl.
*A01H 5/08* (2018.01)

(52) U.S. Cl.
USPC ..... Plt./208
CPC ..... *A01H 5/0893* (2013.01)

(58) Field of Classification Search
USPC ..... Plt./208, 209
See application file for complete search history.

*Primary Examiner* — Susan McCormick Ewoldt
(74) *Attorney, Agent, or Firm* — John Fado; Ariel Atkinson

(57) ABSTRACT

This invention relates to new and distinct cultivar of strawberry plant named 'Marys Peak'. The new cultivar is primarily characterized by its mid-late season ripening, and its firm medium-large, conical to slight wedge shaped fruit that have excellent processing characteristics including red internal and external color, sweet flavor, and easy calyx removal, as well as vigorous, upright and open plants that are productive and efficiently hand-harvested.

5 Drawing Sheets

Latin name of the genus and species of the plant claimed: 'MARYS PEAK' is a new strawberry plant that is *Fragaria xananassa* Duchesne ex Rozier.

Variety denomination: The new strawberry plant claimed is of the variety denominated 'Marys Peak', *Fragaria xananassa* Duchesne ex Rozier.

BACKGROUND OF THE INVENTION

The present invention relates to a new and distinct strawberry cultivar designated 'Marys Peak' and botanically known as *Fragaria xananassa* Duchesne ex Rozier. This new strawberry cultivar was discovered in Corvallis, Oreg. in June 2002 and originated from a cross between the female parent 'Pinnacle' (unpatented) and the male parent 'ORUS 1723-3' (unpatented). The original seedling of the new cultivar was asexually propagated via tissue culture and vegetative cuttings since 2002 in Benton County, Oreg. The present invention has been found to be stable and to reproduce true to type through successive asexual propagations.

BRIEF DESCRIPTION OF THE PHOTOGRAPHS

The accompanying color photographs show typical specimens of the new cultivar at various stages of development as nearly true as it is possible to make in color reproductions.

DETAILED DESCRIPTION OF THE NEW CULTIVAR

Figure 1:
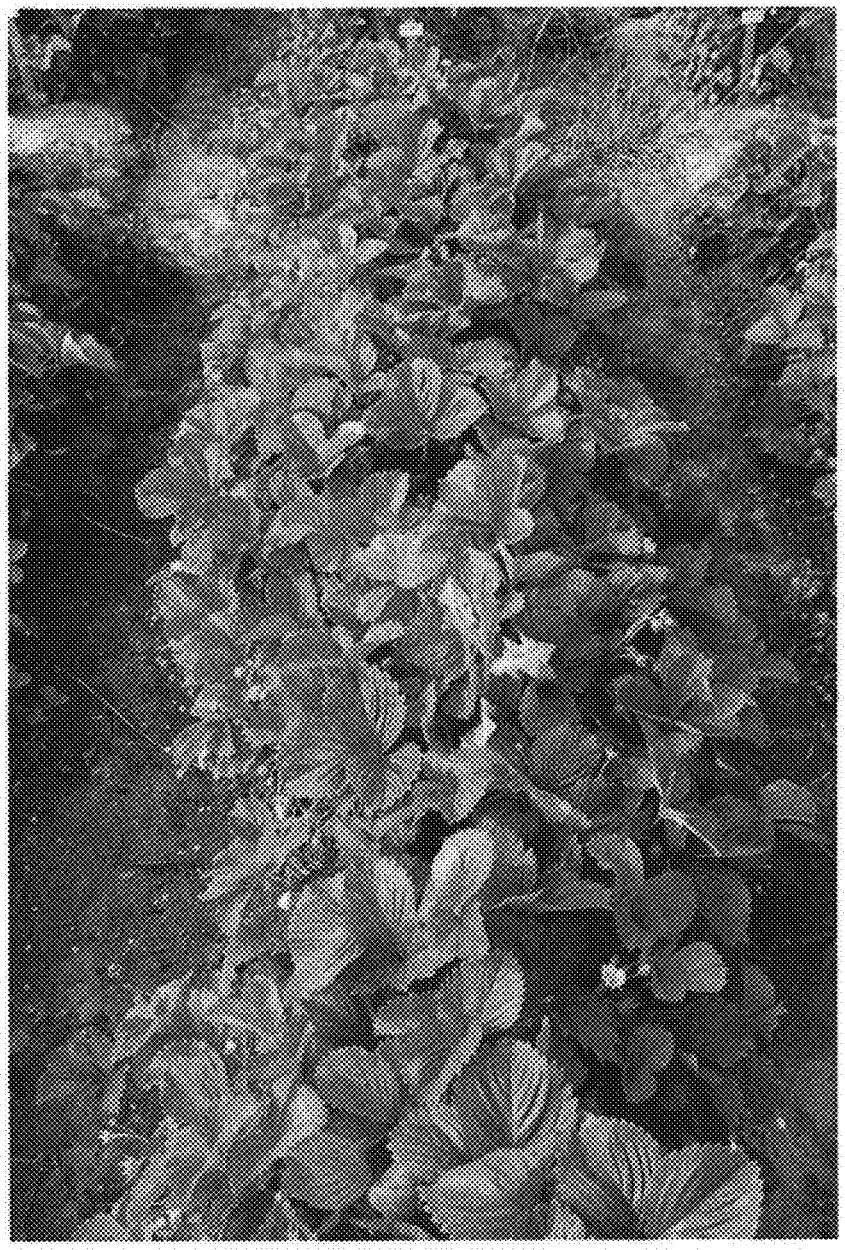
FIG. 1 shows overall plant habit.
Figure 2:
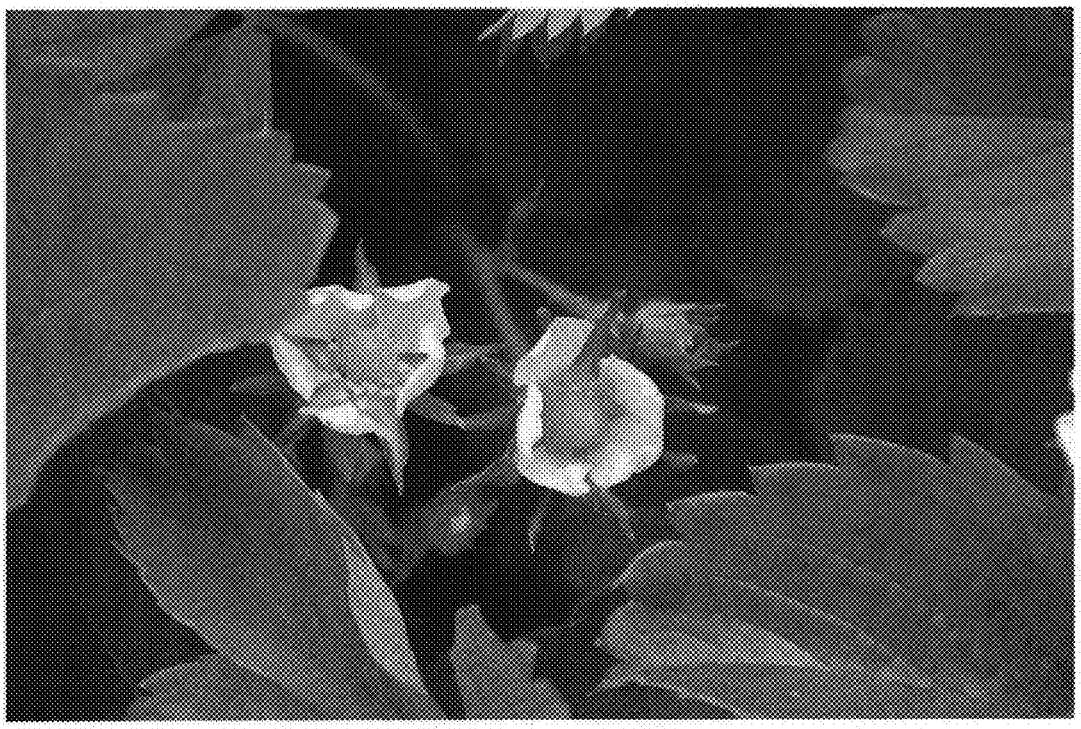
FIG. 2 shows the flower morphology.
Figure 3:
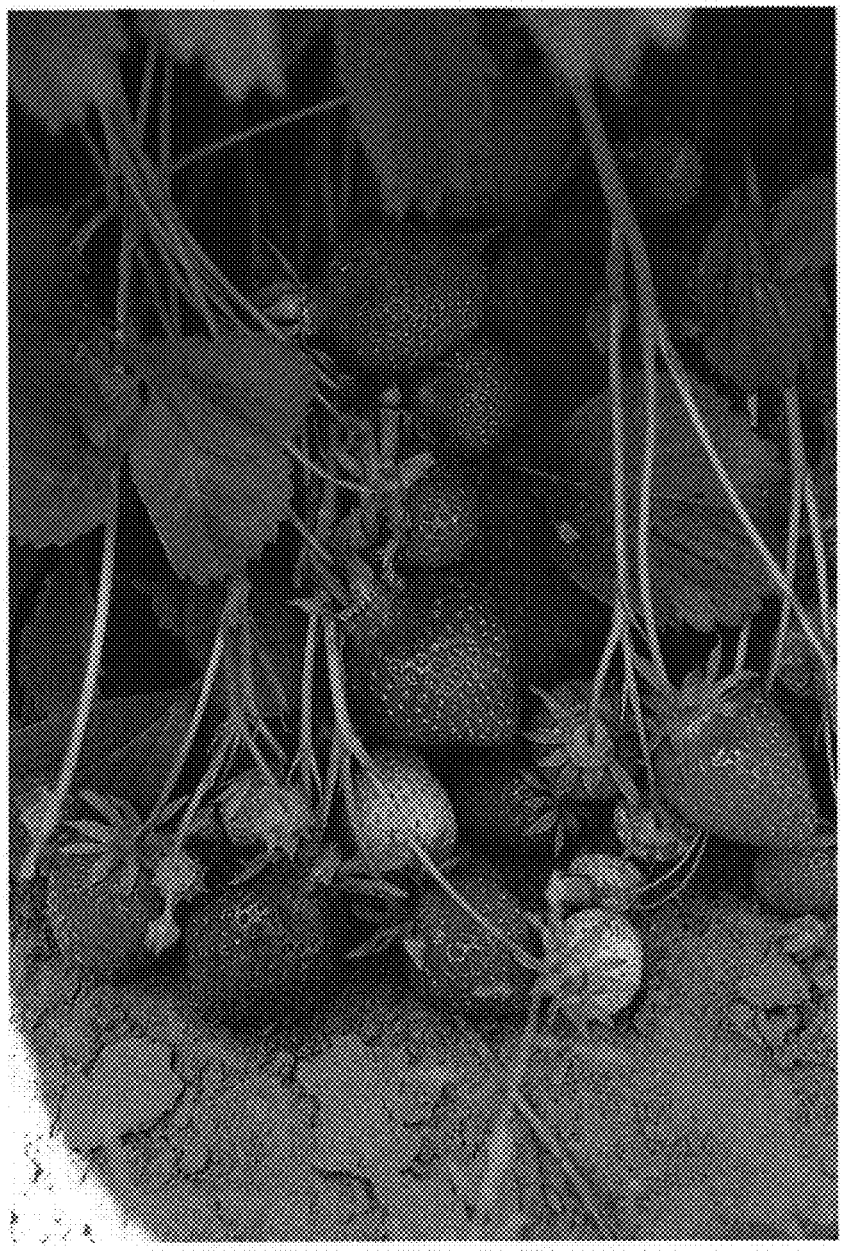
FIG. 3 shows flower trusses with fruit in a range of ripening stages.
Figure 4:
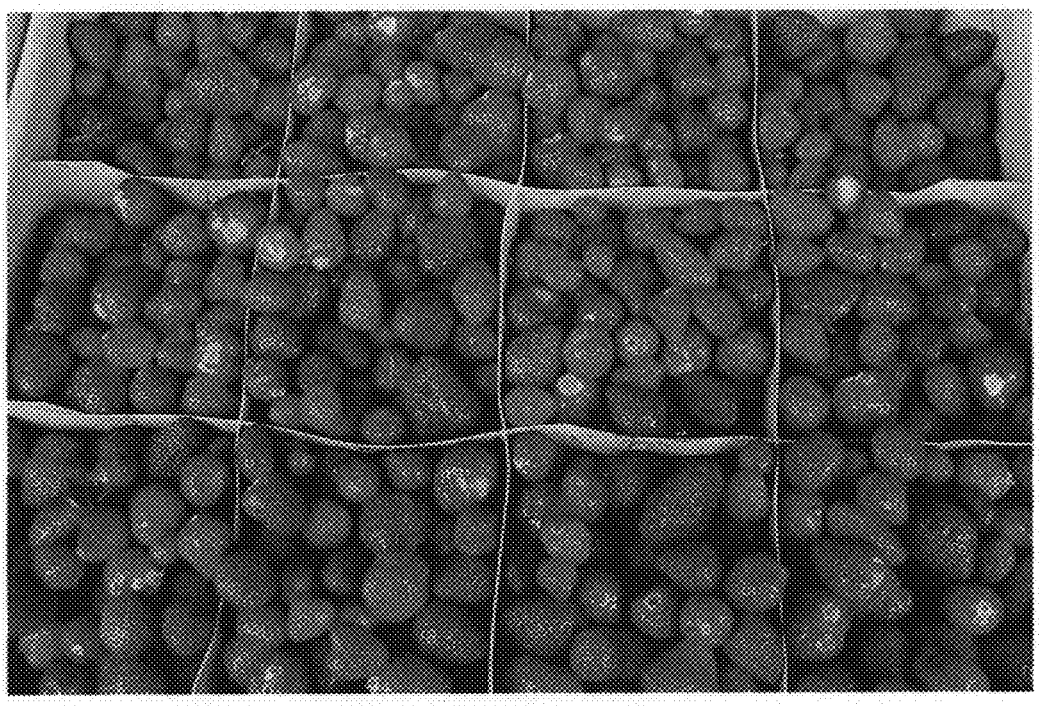
FIG. 4 shows typical fruit after harvest for processing market.
Figure 5:
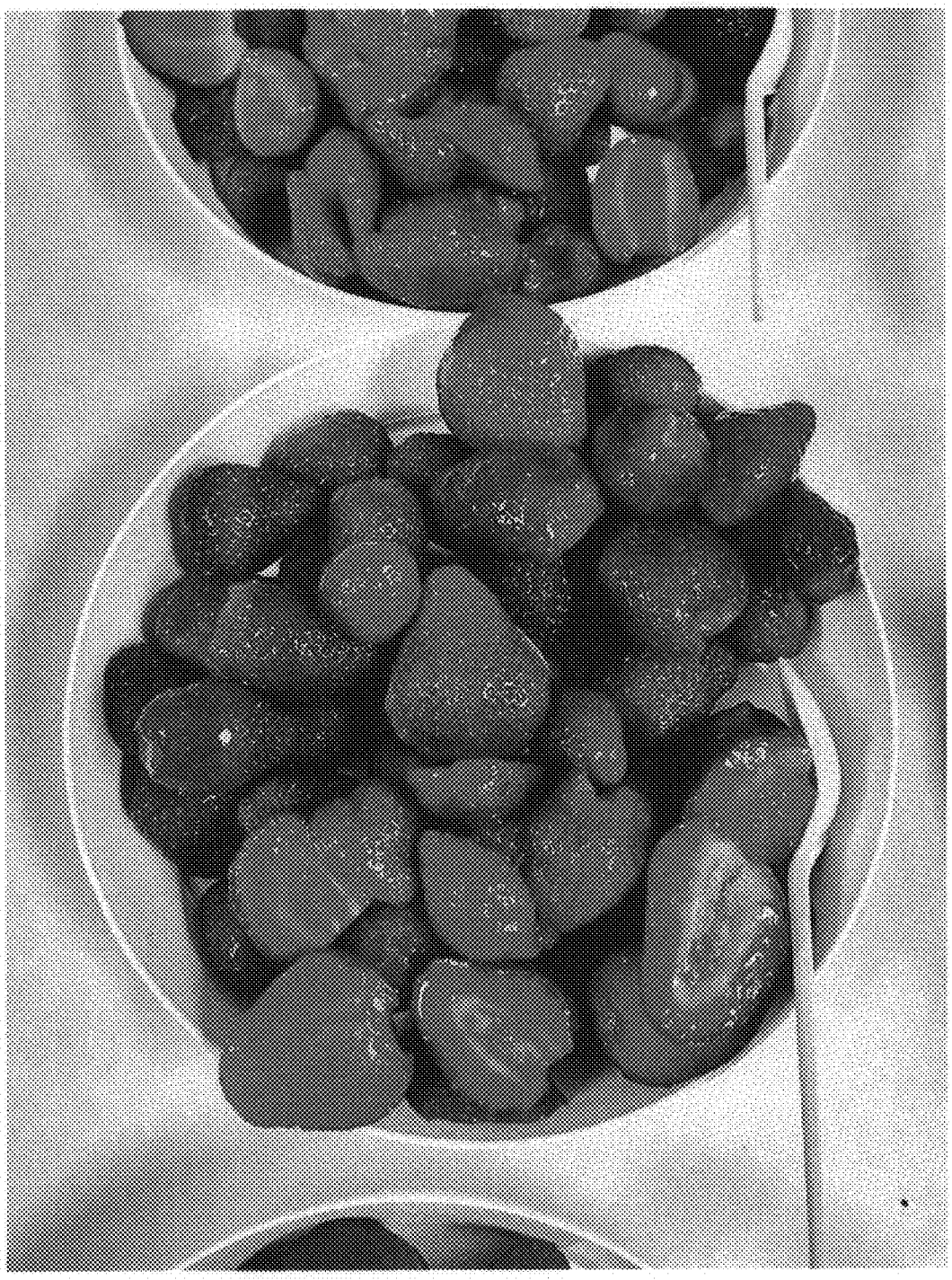
FIG. 5 shows typical entire and sliced fruit after freezing and thawing.

The following description of 'Marys Peak' is based on observations taken from 2004 to 2016 growing seasons in trials in Corvallis and Aurora, Oreg. This description is in accordance with UPOV terminology. Color designations, color descriptions and other phenotypical descriptions may deviate from the stated values and descriptions depending upon variation in environmental, seasonal, climatic and cultural conditions. 'Marys Peak' has not been observed under all possible environmental conditions. The botanical description of 'Marys Peak' was taken from plants one year after establishment in the field. Color terminology follows The Royal Horticultural Society Colour Chart. London (R.H.S.) ($5^{th}$ edition, 2007).

DETAILED BOTANICAL DESCRIPTION

Table 1 shows plant characteristics of the new cultivar. Plant characteristics include plant height, diameter, number of crowns per plant, habit, density of individual plants and vigor.

TABLE 1

Plant Characteristics of 'Marys Peak'.

| Characteristic | Marys Peak |
|---|---|
| Plant height | 16.0 cm |
| Plant diameter | 29.7 cm |
| Number of crowns/plant | 2.6 |
| Habit | Upright, open globose |
| Density of individual plant | Low to medium |

TABLE 1-continued

Plant Characteristics of 'Marys Peak'.

| Characteristic | Marys Peak |
|---|---|
| Vigor | Medium to strong |
| Winter hardiness | Comparable to 'Tillamook' (unpatented), 'Totem' (unpatented) and 'Hood' (unpatented) |

Table 2 shows leaf characteristics of the new cultivar. Leaf characteristics include leaf type, leaf length, leaf width, terminal leaflet length, terminal leaflet width, terminal leaflet length to width ration, leaf margins, shape of teeth, leaf serrations per leaflet, upper and lower leaf surface color, number of leaflets, terminal leaflet apex shape, terminal leaflet base shape, glossiness upper side leaf surface, texture upper side leaf surface, texture underside leaf surface and leaf arrangement.

TABLE 2

Leaf Characteristics of 'Marys Peak'.

| Characteristic | 'Marys Peak' |
|---|---|
| Leaf type | Semi-evergreen leaves will die back to ground in severe winters |
| Leaf shape | Ovate |
| Leaf length | 10.00 cm |
| Leaf width | 15.33 cm |
| Terminal leaflet length | 8.91 cm |
| Terminal leaflet width | 7.43 cm |
| Terminal leaflet length/width ratio | 1.2 |
| Leaf margins | Single serration |
| Shape of teeth | Pointed |
| Leaf serrations per leaflet | 17.0 |
| Color mature leaves upper surface | Green Group N 137B |
| Color mature leaves lower surface | Green Group 146B |
| Number of leaflets | 3 |
| Terminal leaflet apex shape | Obtuse |
| Terminal leaflet base shape | Rounded cuneate |
| Glossiness upper side leaf surface | Semi-gloss |
| Texture upper side leaf surface | Very lightly tomentose |
| Texture underside leaf surface | Tomentulose |
| Leaf arrangement | Compound with three leaflets |

Table 3 shows information about the petiole, the petiolule, the bract and the stipule of the new cultivar. This includes petiole length, petiole diameter, petiole pubescence, petiole color, petiolule color, petiolule length, bract frequency, texture petiole, stipule length, and stipule width.

TABLE 3

Foliage Characteristics of 'Marys Peak'.

| Characteristic | 'Marys Peak' |
|---|---|
| Leaf petiole length | 22.66 cm |
| Petiole diameter | 0.35 cm |
| Petiole pubescence | Medium |
| Petiole color | 144D |
| Petiolule color | 144D |
| Petiolule length | 0.89 cm |
| Bract frequency | Typically two |
| Stipule length | 2.39 cm |
| Stipule width | 1.24 cm |

Table 4 shows stolen characteristics of the new cultivar. These characteristics include the number of stolons, the anthocyanin coloration of the stolons, the thickness of the stolons, and the pubescence of the stolons.

TABLE 4

Stolen Characteristics of 'Marys Peak'.

| Characteristic | 'Marys Peak' |
|---|---|
| Stolon number | 11.4 |
| Stolon anthocyanin | Between weak and medium on top surface |
| Stolon thickness (cm) | 0.29 |
| Stolon pubescence | Present, fairly dense |

Table 5 shows inflorescence characteristics of the new cultivar. These characteristics include inflorescence position relative to foliage, flower type, flower size, petal shape, relative petal spacing, petal apex shape, petal margin, petal base shape, petal length, petal width, petal length/width ratio, number of petals, petal color, stigma color, style color, anther color, filament color, and flower truss type.

TABLE 5

Flower and Flowering Characteristics of 'Marys Peak'.

| Characteristic | 'Marys Peak' |
|---|---|
| Inflorescence position | Between level with and above |
| Flower type | Complete simple |
| Flower diameter | 3.52 cm |
| Petal shape | Orbicular |
| Petal spacing | Overlapping |
| Petal apex shape | Rounded |
| Petal margin | Entire |
| Petal base shape | Rounded |
| Petal length | 1.62 cm |
| Petal width | 1.35 cm |
| Petal length/width ratio | 1.14 |
| Petal count | 5.0 |
| Petal color | White Group 155C |
| Stigma color | Yellow Group 2B |
| Style color | Yellow Group 2B |
| Anther color | Yellow-Orange Group 15B |
| Filament color | Yellow Group 2B |
| Blooming habit | Cyme |

Table 6 shows fruit characteristics of the new cultivar. These characteristics include number of berries per truss, fruiting truss attitude, fruit length, fruit diameter, fruit length/width ratio, fruit weight, relative fruit size, predominant fruit shape, difference in shape between primary and secondary fruit, band without achenes, evenness of fruit surface, top color, non-blush side color, blush side color, internal color, achene color, achene count per fruit, insertion of calyx, pose of calyx segments, size of calyx in relation to fruit, ease of calyx removal, firmness of flesh, evenness of flesh color, distribution of flesh color, sweetness, acidity, Brix, pH, titratable acidity, texture when tasted, time of flowering, harvest maturity (50% of plants with ripe fruit), type of bearing, and yield in $1^{st}$ and $2^{nd}$ harvest seasons.

TABLE 6

Fruit and Fruiting Characteristics of 'Marys Peak'.

| Characteristic | 'Marys Peak' |
|---|---|
| Number of berries per fruiting truss | 2.63 |
| Fruiting truss attitude | Between erect and semi-erect |
| Diameter fruit | 3.17 cm |
| Length fruit | 3.97 cm |
| Ratio fruit length/width | 1.29 |
| Weight fruit | 15.40 g |
| Relative fruit size | Medium-large |

TABLE 6-continued

Fruit and Fruiting Characteristics of 'Marys Peak'.

| Characteristic | 'Marys Peak' |
|---|---|
| Predominant fruit shape | Conic, slight wedge |
| Difference in shape between primary and secondary fruits | Slight |
| Band without achenes | Narrow |
| Evenness of fruit surface | Even |
| Color of top of fruit | Red Group 53A |
| Non-blush side color | Red-Purple Group 59A |
| Blush side color | Red-Purple Group 59A |
| Internal flesh color | Red Group 46A |
| Achene color | Greyed-Red Group 180A |
| Achene count | 97.0 |
| Insertion of calyx | Level |
| Pose of calyx segments | Spreading |
| Size of calyx in relation to fruit | Smaller |
| Ease of calyx removal | Easy |
| Firmness of flesh | Very firm |
| Evenness of flesh color | Even |
| Distribution of flesh color | Throughout |
| Sweetness | Strong |
| Acidity | Medium |
| Brix (percent soluble solids) | 8.74 |
| pH | 3.39 |
| Titratable acidity (g citric acid/100 g fruit) | 9.34 |
| Texture when tasted | Fine |
| Time of flowering | Begins mid-late April, ends early-mid May |
| Harvest maturity (50% of plant with ripe fruit) | Mid-June |

TABLE 6-continued

Fruit and Fruiting Characteristics of 'Marys Peak'.

| Characteristic | 'Marys Peak' |
|---|---|
| Type of bearing | Short-day/June-bearing |
| Yield 1st harvest season-kg/hectare | 26,294 |
| Yield 2nd harvest season-kg/hectare | 16,219 |

COMPARISON WITH PARENTAL AND COMMERCIAL VARIETIES

When 'Marys Peak' is compared to female parent 'Pinnacle' (unpatented), the fruit are deeper red, slightly conic to wedge shaped, and more uniformly shaped.

When 'Marys Peak' is compared to the male parent ORUS 1723-3 (unpatented) the fruit are much larger and firmer and the plants have a much more upright and open canopy.

When 'Marys Peak' is compared to the commercial variety 'Totem' (unpatented) and 'Tillamook' (unpatented), 'Marys Peak' has large, firm, lighter colored fruit and an open plant canopy and ripens in the late midseason, 'Totem' has medium sized, soft, dark fruit, and a dense plant canopy and ripens in midseason, and 'Tillamook' has large, firm, lighter colored fruit and an open plant canopy and ripens in early midseason.

We claim:

1. A new and distinct cultivar of strawberry plant as described and shown herein.

* * * * *